United States Patent
Bearman et al.

(10) Patent No.: US 7,471,831 B2
(45) Date of Patent: Dec. 30, 2008

(54) HIGH THROUGHPUT RECONFIGURABLE DATA ANALYSIS SYSTEM

(75) Inventors: Greg Bearman, Pasadena, CA (US); Michael J. Pelletier, La Canada, CA (US); Suresh Seshadri, Cerritos, CA (US); Bedabrata Pain, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 679 days.

(21) Appl. No.: 10/759,808

(22) Filed: Jan. 16, 2004

(65) Prior Publication Data

US 2004/0207731 A1 Oct. 21, 2004

Related U.S. Application Data

(60) Provisional application No. 60/440,462, filed on Jan. 16, 2003, provisional application No. 60/502,542, filed on Sep. 12, 2003.

(51) Int. Cl.
*G06K 9/46* (2006.01)

(52) U.S. Cl. .................. 382/191; 382/207; 382/270; 382/133; 382/232; 382/312; 348/303; 341/155

(58) Field of Classification Search .......... 382/191, 382/207.99, 133, 232, 270, 312; 250/208.1; 257/431; 438/505; 345/7; 348/303; 702/28; 704/219; 710/72; 341/155
See application file for complete search history.

(56) References Cited

U.S. PATENT DOCUMENTS

| | | | | |
|---|---|---|---|---|
| 4,764,963 A * | 8/1988 | Atal | ..................... | 704/219 |
| 5,117,466 A * | 5/1992 | Buican et al. | ................ | 382/133 |
| 5,121,337 A * | 6/1992 | Brown | ..................... | 702/28 |
| 5,805,933 A * | 9/1998 | Takahashi | ..................... | 710/72 |
| 5,821,911 A * | 10/1998 | Jachimowicz | ................ | 345/7 |
| 5,886,659 A * | 3/1999 | Pain et al. | ..................... | 341/155 |
| 5,901,257 A * | 5/1999 | Chen et al. | ................ | 382/312 |
| 5,937,318 A * | 8/1999 | Warner et al. | ................ | 438/505 |
| 5,949,483 A * | 9/1999 | Fossum et al. | ............... | 348/303 |
| 5,982,318 A * | 11/1999 | Yiannoulos | ................ | 341/155 |
| 5,990,469 A * | 11/1999 | Bechtel et al. | ........... | 250/208.1 |
| 5,995,676 A * | 11/1999 | Campbell et al. | ........... | 382/270 |
| 6,181,823 B1 * | 1/2001 | Takahashi | ..................... | 382/232 |
| 6,225,670 B1 * | 5/2001 | Dierickx | ..................... | 257/431 |
| 6,529,276 B1 | 3/2003 | Myrick | | |

FOREIGN PATENT DOCUMENTS

EP 620613 A2 * 10/1994

\* cited by examiner

*Primary Examiner*—Brian Q Le
*Assistant Examiner*—Tsung-Yin Tsai
(74) *Attorney, Agent, or Firm*—Christie, Parker & Hale, LLP

(57) ABSTRACT

The present invention relates to a system and method for performing rapid and programmable analysis of data. The present invention relates to a reconfigurable detector comprising at least one array of a plurality of pixels, where each of the plurality of pixels can be selected to receive and read-out an input. The pixel array is divided into at least one pixel group for conducting a common predefined analysis. Each of the pixels has a programmable circuitry programmed with a dynamically configurable user-defined function to modify the input. The present detector also comprises a summing circuit designed to sum the modified input.

48 Claims, 10 Drawing Sheets

Table 1. Synthetic Mixture Spectra

Synthetic Mixture Spectra

| | 1 | 2 | 3 | 4 | 5 | 6 | 7 | 8 | 9 | 10 | 11 | 12 |
|---|---|---|---|---|---|---|---|---|---|---|---|---|
| %YFP | 50 | 1 | 19 | 15 | 5 | 10 | 0 | 0.5 | 1 | 2 | 4 | 0 |
| %CFP | 10 | 50 | 1 | 19 | 15 | 5 | 10 | 10 | 10 | 10 | 10 | 10 |
| %DiI | 5 | 10 | 50 | 1 | 19 | 15 | 10 | 10 | 10 | 10 | 10 | 10 |
| %GFP | 15 | 5 | 10 | 50 | 1 | 19 | 10 | 10 | 10 | 10 | 10 | 10 |
| %EtBr | 19 | 15 | 5 | 10 | 50 | 1 | 60 | 60 | 60 | 60 | 60 | 60 |
| %RFP | 1 | 19 | 15 | 5 | 10 | 50 | 10 | 9.5 | 9 | 8 | 6 | 0 |
| Total | 100 | 100 | 100 | 100 | 100 | 100 | 100 | 100 | 100 | 100 | 100 | 100 |
| Mixture # | 1 | 2 | 3 | 4 | 5 | 6 | 7 | 8 | 9 | 10 | 11 | 12 |

FIG. 5B

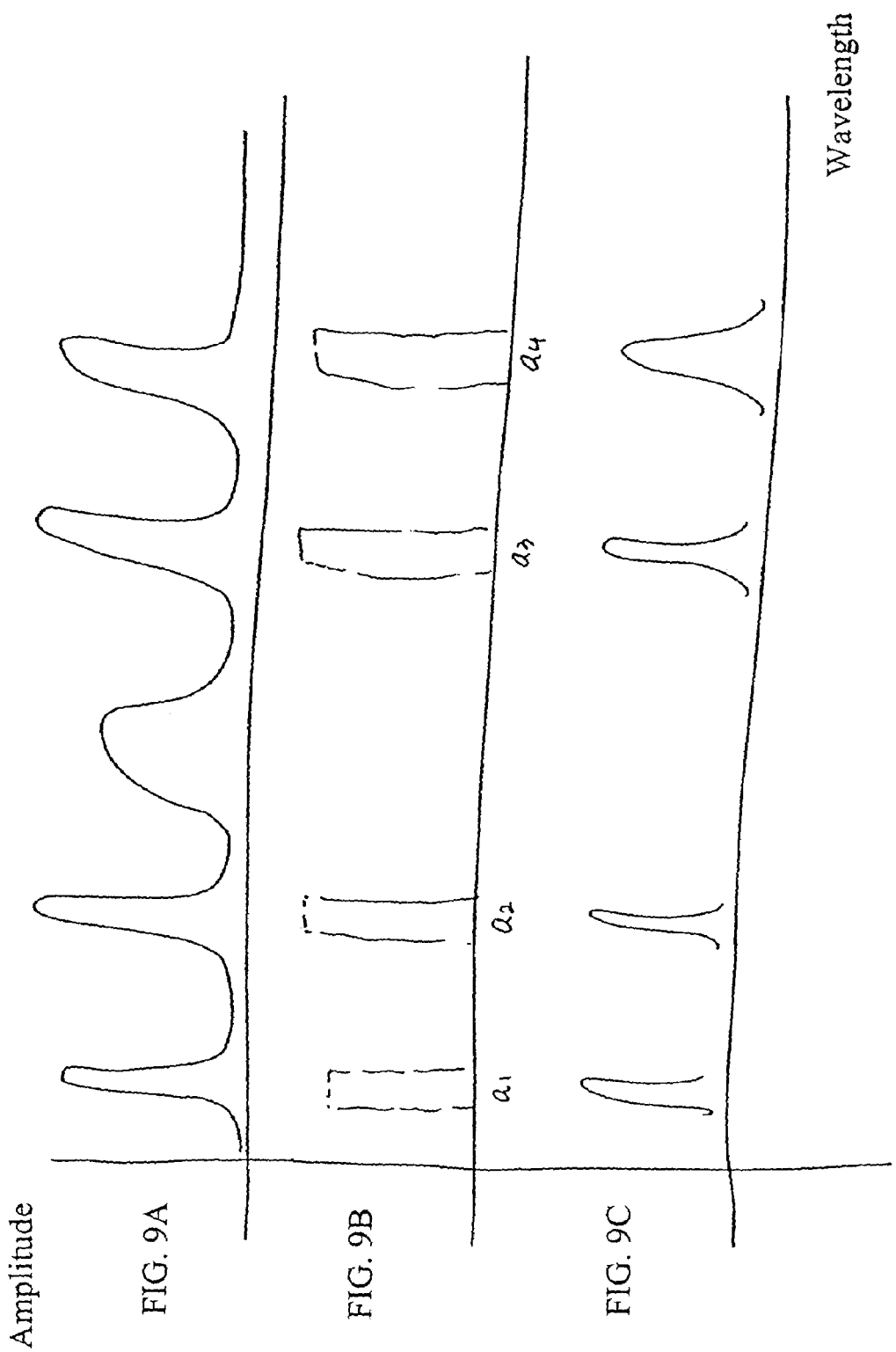

HIGH THROUGHPUT RECONFIGURABLE DATA ANALYSIS SYSTEM

CROSS-REFERENCE TO RELATED APPLICATION(S)

This application claims priority based on provisional patent application No. 60/440,462, filed Jan. 16, 2003 and 60/502,542, filed Sep. 12, 2003, the entire disclosures of which are hereby incorporated by reference.

STATEMENT REGARDING FEDERALLY SPONSORED RESEARCH OR DEVELOPMENT

The invention described herein was made in the performance of work under a NASA contract NAS7-03001 and is subject to the provisions of Public Law 96-517 (35 U.S.C. 202) in which the Contractor has elected to retain title.

FIELD OF THE INVENTION

The present invention relates generally to data analysis, and more specifically to programmable data analysis system for various applications.

BACKGROUND OF THE INVENTION

Spectra often consist of hundreds to many thousands of intensity measurements as a function of wavelength or scattering angle. This information can be used to identify and quantitate multiple target species in complex matrices of samples of interest, which may include flowing streams (e.g., flow cytometry) or any sort of microscopy, whether full field imaging or confocal, including scanning and Nipkow disk.

Spectral analysis to identify and analyze target species from a sample is usually performed by sending the light from a sample through a spectrometer or monochromator which disperses the photon signal onto a detector. Each target generates a unique spectrum that is then received by the detector and measured. Examples of commercial instruments using this approach include Raman gas analyzers, NIR gas analyzers, flow cytometers, fluorescence microscopes, Raman imaging microscopes, and particle size analyzers. In some cases, the monomchromator can be replaced by discrete bandpass filters, as in the case of fluorescent probes that have been designed to fluoresce at discrete wavelengths.

In many cases, the desired analytes spectra may overlap, as in the case of many biological probes such as fluorescent probes widely used in molecular biology, fluorescence microscopy and flow cytometry. In these cases, the problem is how to increase the number of analytes (probes) and still be able to separate them spectrally for both detection and quantitation. One approach has been to acquire the complete spectrum of the system and then deconvolve the summed spectrum of each analyte; such techniques are particularly useful for fluorescent biological probes as fluorescence adds linearly. This means that the measured spectrum is the linear sum of each analyte spectrum times its concentration. Linear unmixing can deconvolve the measured spectrum to recover whether and how much of each analyte is present. This is done offline, after acquisition of the complete spectrum. This approach can also be applied to images as well. This technique has been demonstrated to separate, without cross talk, fluorescent probes that differ by only 5 nm in their peaks. The spectra also can be analyzed using powerful multivariate mathematical methods. These methods can provide accurate quantitative determinations of multiple target species in similar cases when the spectral differences between species in the sample are too subtle for successful analysis using bandpass filters, dichroics, longpass and shortpass filters or combinations of such devices.

For some probes or analytes, the signals are separated enough spectrally that discrete bandpass filters can be used, as in commercially available fluorescence microscopy filter cubes. A bandpass filter transmits light that is characteristic of the target species, and not produced by the other components of the sample. More generally though, many desired probes such as gene reporters overlap significantly spectrally. Also, by increasing the number of probes to increase the number of analytes per measurement, the spectral signatures would inherently get closer and begin to overlap. Since the desired spectral signals in these cases are so close, discrete optical bandpass filters cannot separate the analytes without crosstalk that degrades quantitation and classification of particular analytes. The limitation of this approach is that the entire spectrum has to be acquired and then subjected to mathematical analysis. Analysis rates are limited by the time to readout the data from the detector and then perform the mathematical analysis.

Thus, a need exists for a system and method for continuously identifying and analyzing multiple target species in real time by utilizing all the analytically useful information in the spectrum.

SUMMARY OF THE INVENTION

Briefly, the present invention relates to a system and method for performing rapid and programmable analysis of various types of data. In one aspect, the present invention relates to a reconfigurable detector comprising at least one array of a plurality of pixels, where each of the plurality of pixels is capable of being selected to receive and read-out an input. The input may be fluorescence spectrum, light scattering angles, or different Fourier frequencies from samples, such as flowing streams, bead assays, cells, tagged cells, and raster-scanned static sample. The pixel array may be one, two, or multi-dimensional array. The pixel array may be divided into multiple pixel groups, each of which has at least two pixels, for conducting a common predefined analysis. Each of the plurality of pixels has a programmable circuitry, each of which is programmed with a dynamically configurable user-defined function that adjusts the weighting of the signal level in each pixel using analog or digital representation.

In one embodiment, the input is modified by cross-correlating the received input with the respective user-defined function for each selected pixel. In this embodiment, cross-correlation is achieved by simultaneously multiplying the received spectrum with the user-defined function for each selected pixel and serially summing the product to generate a single scalar output.

In another embodiment, the detector may also include a summing circuit in communication with the plurality of programmable circuits. In such an embodiment, the summing circuit is designed to sum the modified inputs from the common pixel group in a single binning instruction to generate a single scalar output for the pixel group. In one embodiment, the summing circuit performs the inner or dot product computation. In another embodiment, the detector has more than two pixels groups, each group having a plurality of independent user defined function associated therewith.

In some embodiments, the detector comprises the pixel array, a user-defined function template and computational units arranged together, or separately depending on the applications and design constraints. Thus, the template and computational units can be in front of, behind or integrated within the pixel. In one embodiment, digital control and timing logic or analog processing and communications circuits are included in this arrangement.

In another aspect of the invention, two dimensional filtering can be used to achieve higher throughput or multiple parameter detection. In this aspect, each pixel has two programmable circuitries operating in parallel. Each programmable circuitry is programmed with a dynamically configurable user-defined function. Two summing circuits are associated with the programmable circuits to perform inner product computation of the modified inputs in a single binning instruction.

BRIEF DESCRIPTION OF THE DRAWINGS

These and other features and advantages of the present invention will be better understood by reference to the following detailed description when considered in conjunction with the accompanying drawings wherein:

FIG. 5B depicts a table listing mixture compositions of the mixtures of FIG. 5A.

FIG. 9A depicts an incoming spectra of an excited sample interest.

FIG. 9B depicts bandpass filters configured by user-defined functions according to one embodiment of the invention.

FIG. 9C is a resultant spectrum of the incoming spectra of FIG. 9A after passing through the bandpass filters of FIG. 9B.

DETAILED DESCRIPTION OF THE INVENTION

The present invention provides a real-time, continuous, reconfigurable analysis system for various applications, such as high throughput screening, cytometry and bead assay for cell sorting (e.g., cancer detection, blood separation, etc.), and spectroscopic imaging. The present invention can also be useful for other applications, such as, image processing, spatial and spectral filtering, as well as determination of shape, size and/or orientation of point particles (e.g. molecules, cells, granular material) and extended objects in robotic vision, target tracking, medical imaging, biometrics or similar applications that utilize computation of inner or dot products in whole or in part in time, space, spectral or fourier domains.

Figure 1:
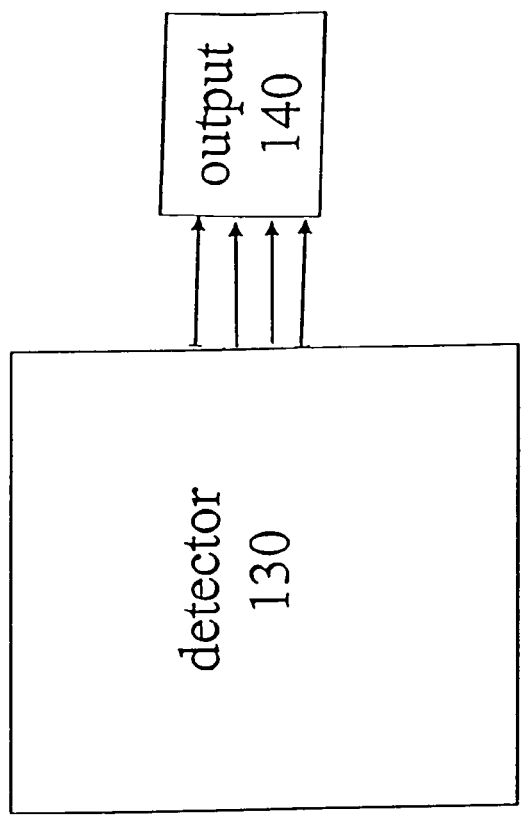
FIG. 1 is a schematic depiction of an optical analysis system according to one embodiment of the present invention.
Figure 1:
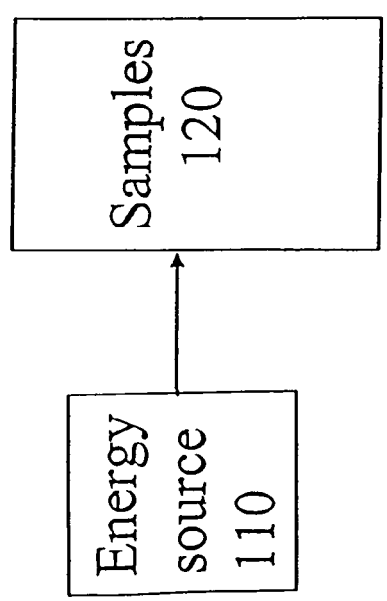

FIG. 1 shows a schematic depiction of one embodiment of an optical analysis system 100 according to the present invention. In the depicted embodiment, the system 100 comprises an energy source 110, a sample of interest 120, a detector 130, and an output 140. The energy source 110 excites or illuminates the sample of interest 120. Light interacts with the sample of interest and is translated into spectra 150, a set of intensity measurements in a function of wavelength or scattering angles, via a spectrograph, collimator or some other conventional instrument. The spectra 150 is then transmitted to and received by the detector 130, which in turn outputs a single scalar output 140 indicative of the measured spectra.

Because the present invention can be implemented for both spectroscopic applications and non-spectroscopic applications, the type of spectrum received by the detector 130 may vary depending on a specific application. Accordingly, the energy source 110 may include any known method of exciting a sample, including electromagnetic radiation of any wavelengths, such as, lasers, fluorescence electricity sources, elemental particles, or ions. Likewise, the sample of interest 120 may comprise any analyte of interest, such as, for example, flowing streams, bead assays, cells, tagged cells, and raster-scanned static samples. For spectroscopic applications, such as fluorescence emission, phosphorescence emission, luminescence emission and electroluminecense, the light spectrum as a function of wavelength is directed to the detector. For non-spectroscopic application, particle size and shape can be discriminated in real time by measuring scattered light intensity (e.g., spectrum) as a function of scattering angle or Fourier frequencies.

As shown in FIG. 1, the present invention uses an array detector 130, which can detect any of the energy sources mentioned above. In one preferred embodiment, the detector 130 is an APS (active pixel sensor). Although the detector may contain hundreds to millions of arrayed pixels, there is no number or dimensionality requirement to implement the analysis system of the present invention. Moreover, the pixels may or may not be provided from the same chip. Although the pixels may be physically separated in different chips, they can still form an array of pixels by connecting them via a wire or some other means of connection. Regardless of the number of pixels or the location of the pixels, in the current system, each pixel has its own programmable circuitry that is programmed to perform high-speed real-time inner or dot product computation, which includes cross-correlation computation. The term "cross-correlation" refers to the value of the cross-correlation function at zero delay. More specifically, each pixel has an associated user-defined function, which resides in the programmable circuitry of the associated pixel to modify or cross-correlate the received spectrum according to a desired analysis scheme in real time. In one embodiment, the desired analysis scheme can be changed by reconfiguring the user-defined function, which in turn is reprogrammed into the programmable circuitry without requiring any changes to the hardware of the circuitry.

Figure 2:
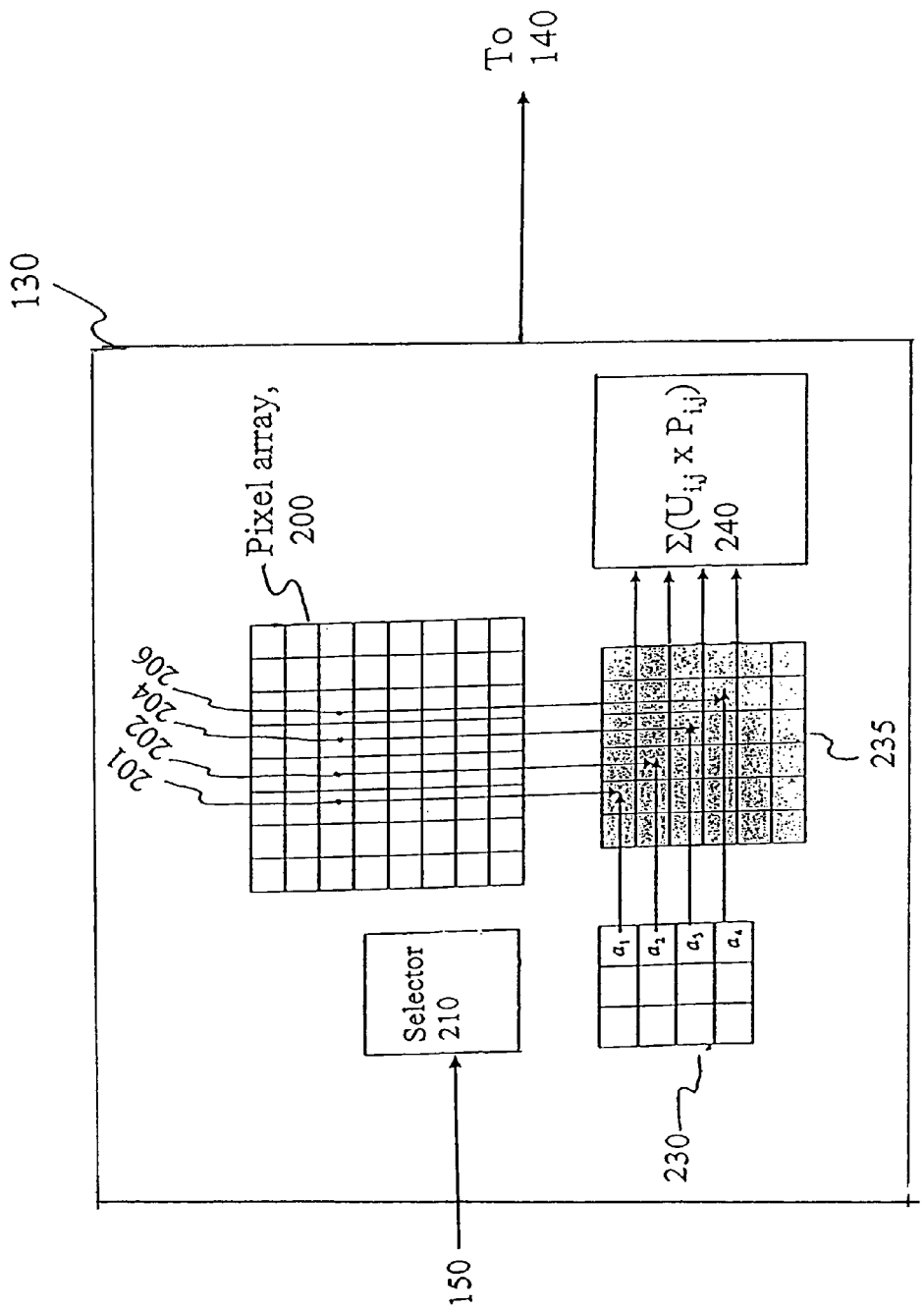
FIG. 2 is a schematic diagram illustrating one exemplary embodiment of a reconfigurable detector included in the optical analysis system of FIG. 1 wherein m and n of the pixel array each equal eight.

FIG. 2 shows a detailed depiction of the detector 130 wherein m and n of the pixel array each equal eight in accordance with one embodiment of the invention. In this embodiment, the detector 130 includes one or more arrays of pixels 200, comprising a plurality of pixels, such as 201, 202, 204, 206, each of which has an associated programmable circuitry that is programmed with a user-defined function to carry out the designed analysis. The detector also comprises a pixel selector 210 that receives commands from a central processor (not shown) to select a specific group of arrayed pixels. A memory (not shown), such as a dynamically addressable random access memory, may be included in the detector to hold read-outs of the selected pixels for analysis.

In one embodiment, as shown in FIG. 2, the programmable circuitries of the pixels collectively include a dynamically adjustable user-defined function template 230, holding the user-defined function (e.g., $a_1$, $a_2$, $a_3$, $a_4$ as shown in FIG. 2) for each selected pixel. The programmable circuitries also collectively include an inner product computational unit 235 performing inner or dot product computation in whole or in part (e.g., for auto-correlation or cross-correlation). More specifically, the inner product computation unit 235 performs $U_{i,j} \times P_{i,j}$, where $U_{i,j}$ is the user defined function for the associated pixel at ith row and jth column in the pixel array 200, and P is the spectrum intensity measurement for the associated pixel $P_{i,j}$. Digital timing and control circuits as well as analog processing, readout and communications circuits may also be included in the detector. The programmable circuitries comprise at least one summing circuit 240 designed to sum the products outputted from the plurality of programmable circuitries to produce a single scalar output.

In some embodiments, the user-defined function template and computational units can be arranged together with the pixel array, or separately from the pixel array on the same chip depending on applications and design constraints. Thus, the template and computation units can be in front of, behind or integrated within the pixel array. In another embodiment, the pixel array, the template, and the computational units are placed in separate chips, but are integrated via connections between the chips (e.g., bump bonding or 3-D chip integration). Regardless of specific arrangements, whether on the same chip or on separate chips, the inner product computation, in whole or in part, is performed either simultaneously during the signal integration time or prior to readout of the signal from the chip. Digital timing and control circuits as well as analog processing, readout and communications circuits may also be included in various arrangements of the detector.

Referring again to FIG. 2, in one embodiment, the pixel selector 210 is a logic circuitry that receives commands from the central processor to select an appropriate set of arrayed pixels (a pixel group) from the array of pixels 200 that receive the spectrum 150 within the emission band associated with the spectrum of the target species.

In short, the pixel array 200 may be divided into one or more pixel groups for a common predefined analysis, such as a particular spectroscopic analysis or non-spectroscopic analysis. Each pixel group in turn comprises at least two arrayed pixels and is utilized to analyze a single species. For analysis of multiple species, two or more pixel groups, where each group has at least two arrayed pixel and has an associated group of independent user-defined functions, are utilized. In one implementation, the pixel array 200 is a 1-dimensional array having a single row of pixels. In a typical implementation, the pixel array 200 is a 2-dimensional array having m rows and n columns of pixels, where $m \leq n$.

As discussed above, to perform an analysis, each pixel is associated with a programmable circuitry programmed with a user defined function. The user-defined function comprises of a function that will selectively pick out the spectrum of the target species from the spectrum of the other species in a sample of mixture by adjusting the weighting of the signal level in each pixel using analog or digital representation.

For example, in the one embodiment, the user-defined function programs the programmable circuitry to perform as a simple bandpass filter consisting of a non-zero gain at the frequencies of the spectral bandpass of the target species, and zeros everywhere else. In this embodiment, characteristics of the bandpass are determined by the spectrograph resolution of the target species and the user-defined function derived from the spectrograph resolution of the target species. Because of the large number of pixels and their associated user-defined functions that can be handled by the detector, the bandpass can be much narrower, thus more sensitive than that of commonly used single-element filters such as thin film dielectric interference filters. In addition, the filter characteristics can be changed by reconfiguring the user-defined functions and reprogramming the programmable circuitry with the reconfigured user-defined functions. Such bandpass filtering is equivalent to cross-correlating the user-defined functions with the measured spectrum from the selected pixels. The output of the bandpass filter or the cross-correlator results in a signal proportional to the concentration of the target species.

As discussed above, a set of user-defined functions having a gain of one where the target species contributes intensity and zeros everywhere else will produce cross-correlation intensities proportional to the target species concentrations. For example, the Raman spectrum of oxygen in air has one major Raman band due to oxygen and one due to nitrogen. A user-defined function with a gain of one corresponding to the detector pixels at the oxygen Raman band location and zeros everywhere else would provide a cross-correlation signal proportional to the concentration of oxygen in air. In one embodiment, for example, the Raman spectrum of oxygen may work as the user-defined function. In turn, changing the user-defined function from an oxygen Raman spectrum to a nitrogen Raman spectrum would effectively change the detector from an oxygen sensor to a nitrogen sensor with no changes in hardware.

Figure 3:
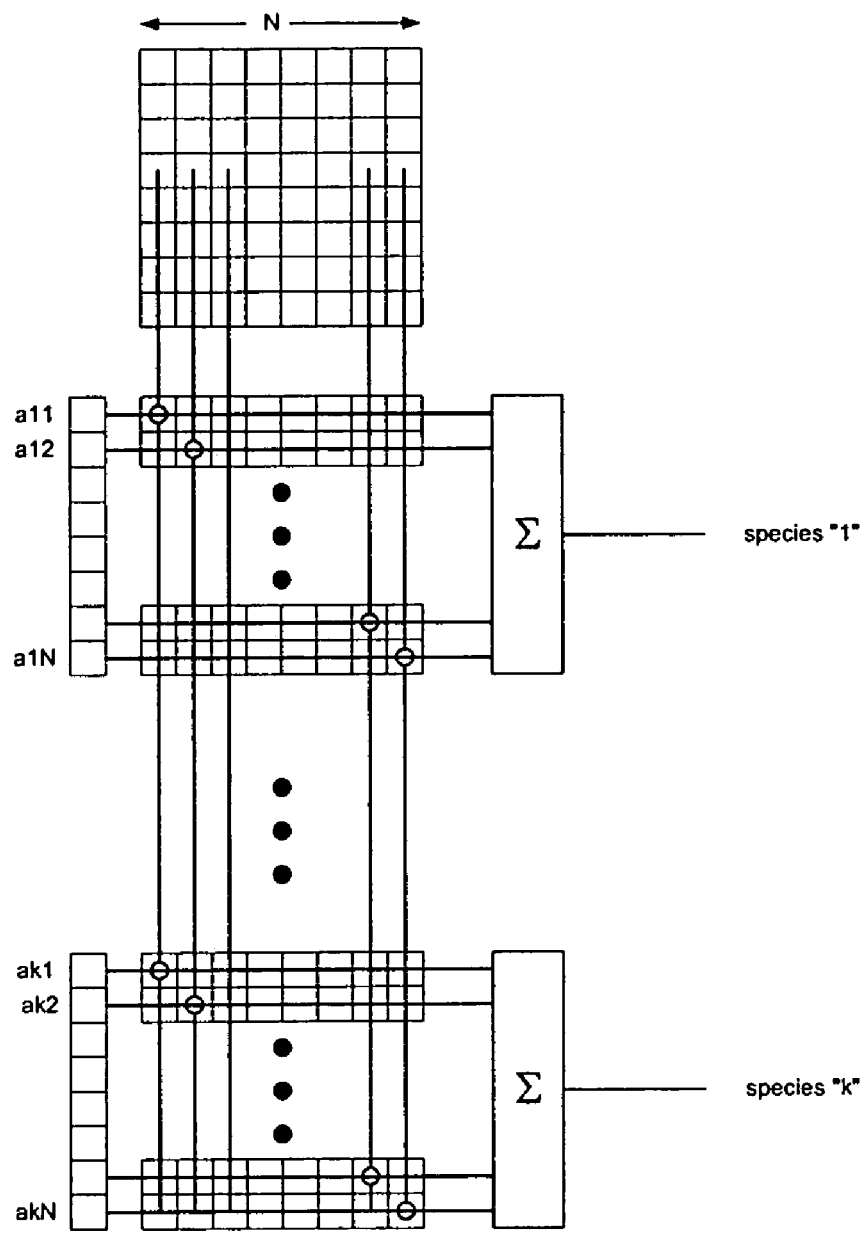
FIG. 3 is a schematic diagram illustrating one embodiment of two-dimensional filtering in accordance with aspects of the inventors.

In one embodiment, two-dimensional filtering can be used to achieve higher throughput or multiple parameter (e.g. concentration and shape) detection. As shown in FIG. 3, instead of using only one filter, a plurality of programmable filters simultaneously operating in parallel are utilized. Similar to the previous example, a programmable circuitry is programmed to perform as a bandpass filter. In one implementation, to achieve two-dimensional filtering each pixel now has a multiple number of these programmable circuitries, corresponding to the number of different species to be identified.

In one example, the spectral (or angular dispersion) data consists of N channels (corresponding to N pixels), and the two-dimensional filter [F(i,j)] represents K number of filters corresponding to K different species to be identified. Parallel filtering generates K different outputs, corresponding to the concentration of each of the K species. Each filter operates simultaneously with other (K−1) filter in parallel on the image data $v_j$ to generate an output:

$$O_i = \sum_j a_{i,j} \cdot v_j$$

where $a_{i,j}$ are the filter coefficients or user-defined functions.

Since the outputs are generated simultaneously in parallel, this approach enables faster species identification by enabling multiple species identification in one step. For example, in an integration time and sample time of 100 nsec per row of pixels, all K outputs (e.g., K=10) are generated within the same time period, using a K×N two-dimensional filter (N=200 for example). Thus, all K species are identified at a 10 MHz rate. If parallelism were not used, each species would be identified at least K times slower rate, for instance at 1 MHz rate if K=10, since the filter coefficients corresponding to each species would need to be changed after each correlation, and the species will be detected in a serial fashion. Therefore, the use of parallelism and on-chip processing enables higher throughput rates for multiple species than could be carried out either serially and/or through off-chip filtering.

As an example, the oxygen and nitrogen band of the Raman spectrum of air can be determined in one step by using two filters, one filter tuned for oxygen, and the other for nitrogen, and running the two filters simultaneously on the pixel data. This will provide both oxygen and nitrogen concentration simultaneously, unlike the case where the filter coefficients have to be changed serially in time, resulting in significant slow-down of detection, both due to doubling the filtering time, and the time required to change the filter characteristics.

Figure 4:
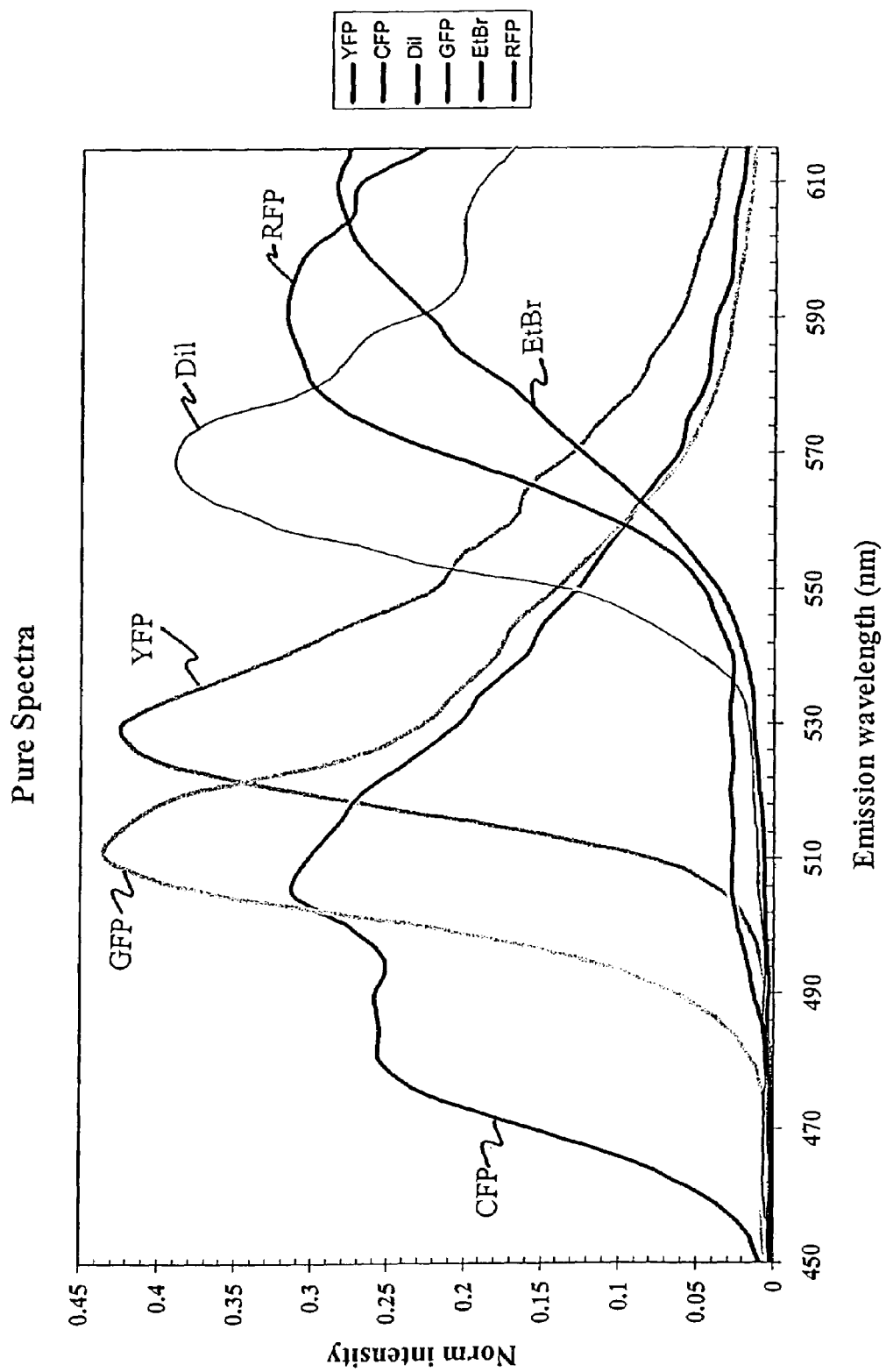
FIG. 4 depicts fluorescence spectra of pure YFP, CFP, Dil, GFP, EtBr, and RFP.
Figure 5A:
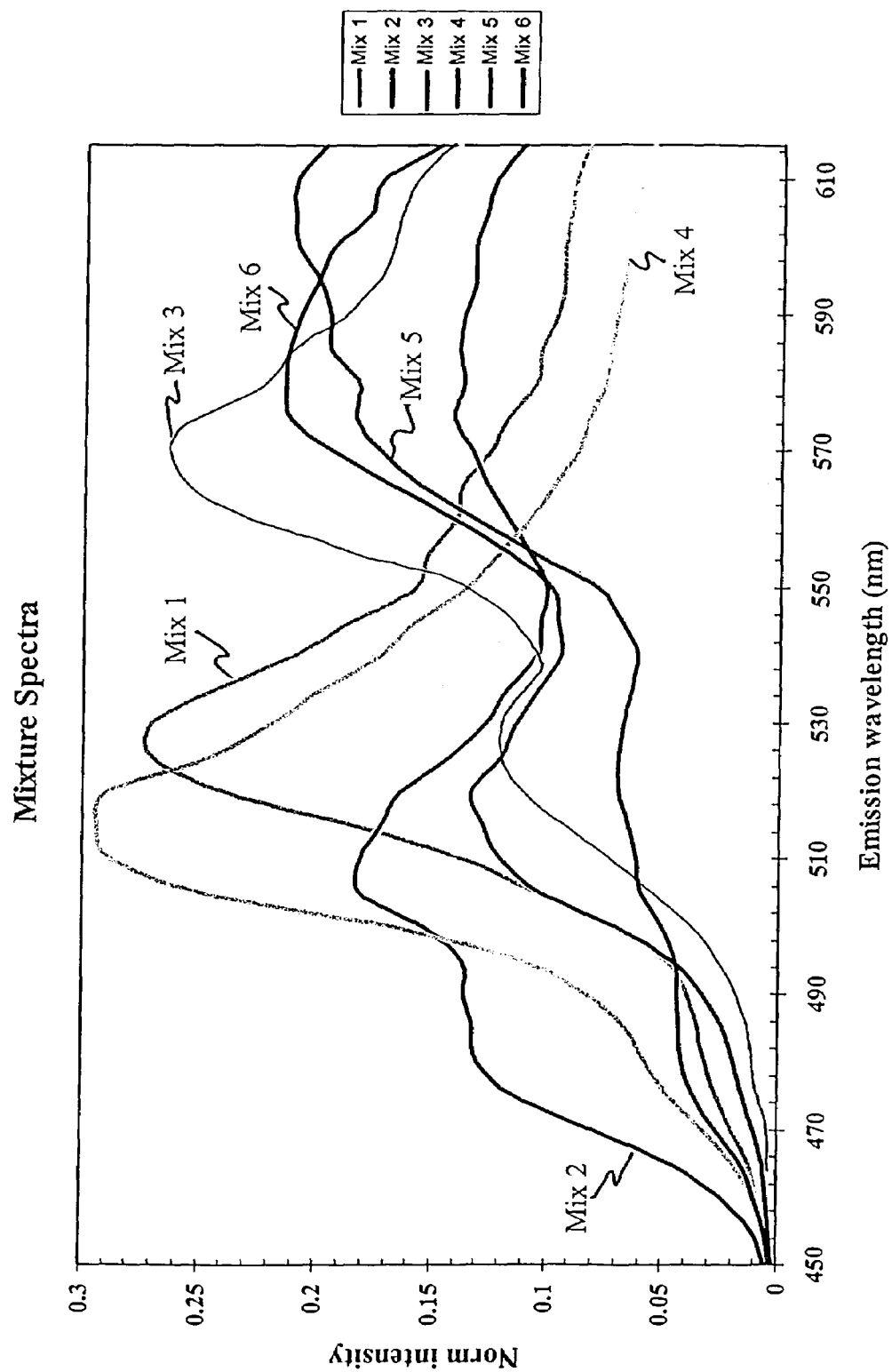
FIG. 5A depicts fluorescence spectra of several mixtures of YFP, CFP, Dil, GFP, EtBr, and RFP.
Figure 6B:
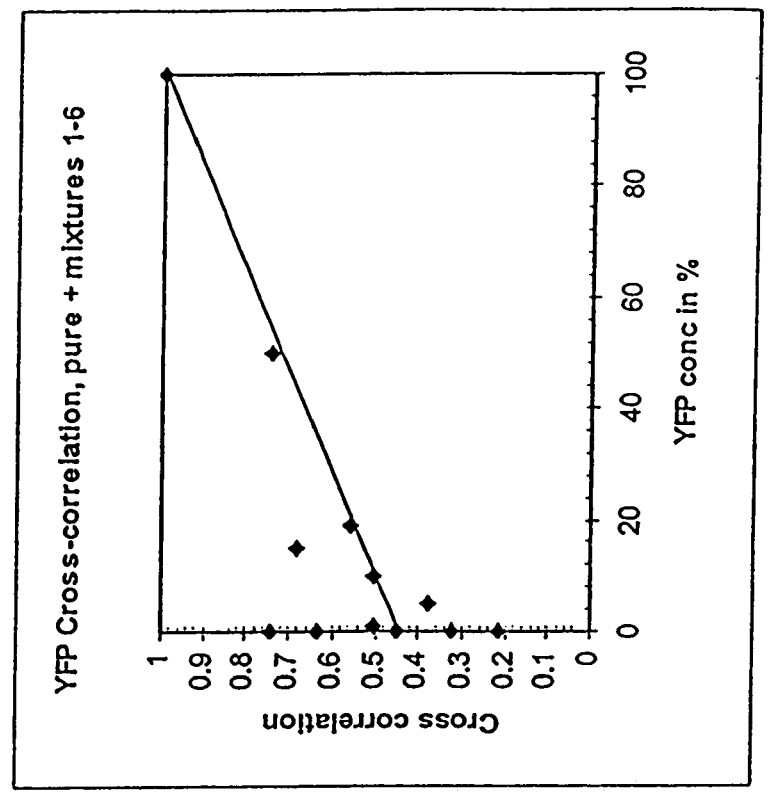
FIG. 6B depicts results of cross-correlating the spectrum of pure YFP with the mixtures 1-6 of listed in the table of FIG. 5B.
Figure 6A:
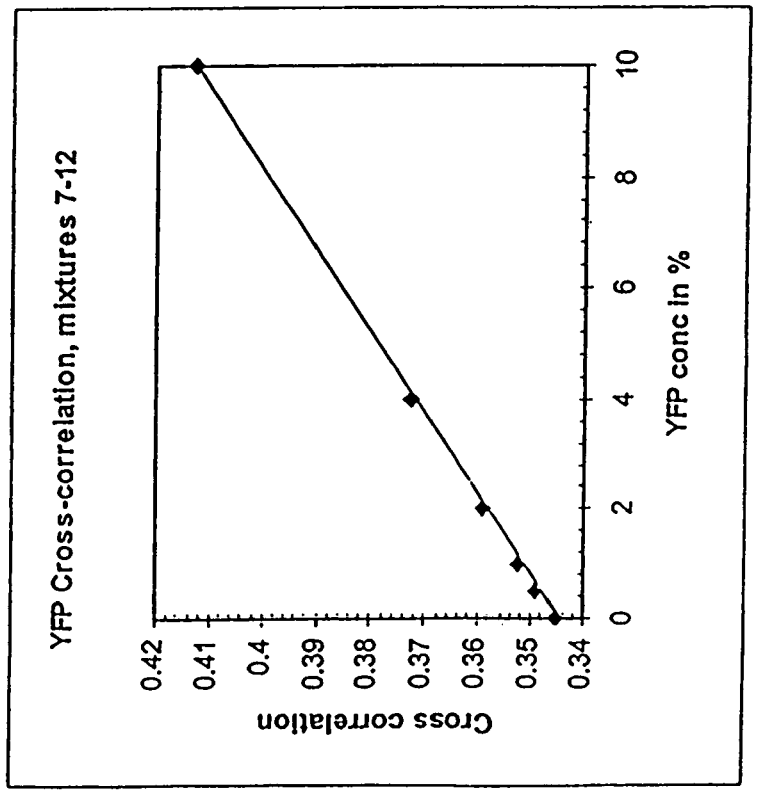
FIG. 6A depicts results of cross-correlating the spectrum of pure YFP with the mixtures 7-12 listed in the table of FIG. 5B.

In some instances, the cross-correlation resultant intensity may not go to zero when the target species concentration goes to zero, since signals contributed by the non-target species may produce non-zero cross-correlation intensity. As long as these signals remain constant, they, however, only create a non-zero intercept in the plot of target species concentration vs. cross-correlation intensity, and do not effect the linearity of the plot. For example, FIG. 4 depicts highly overlapping fluorescence spectra of species yellow Fluorescence Protein (YFP), cyanFP (CFP), dialklycarocynanine (Dil), greenFP (GFP), Ethidium Bromide (EtBr), and redFP (RFP). Fluorescence spectra of several mixtures having different concentration of the above-listed species are depicted in FIG. 5A. Mixture compositions are shown in Table 1 of FIG. 5B. FIG. 6A shows the results of cross-correlating the spectrum of pure YFP with the spectra of mixtures 7-12.

The mixtures 7-12 have an approximately constant spectrum from the non-YFP species, accordingly, the calibration curve of target species YFP concentration vs. cross-correlation intensity of FIG. 6A is linear and predictive of YFP concentration. However, as explained before, the y-intercept is large due to the cross-correlated intensity from the other fluorescent species in the samples.

Although the above example shows results of an analysis for multiple species having constant concentrations, if more than one species are present in the sample, it is not uncommon for multiple species in the sample to have significantly varying concentrations. Any user-defined function for one species will generally produce a non-zero cross-correlation intensity for each of the other species when there is significant spectral overlap among the species in the sample. Referring back to the example, when the same cross-correlation procedure is applied to a sample set consisting of the pure YFP species and mixtures 1-6, the resulting calibration curve, as illustrated in FIG. 6B, is poorly predictive of YFP concentration. Here the composition of each mixtures differs significantly and there is significant spectral overlap among the species in the sample. In this instance, single cross-correlation intensity is then no longer predictive of the target species concentration.

A user-defined function that accurately predicts analyte concentration despite spectral changes caused by other components of the sample can be found using multivariate analysis methods. The spectral variance in a training set of samples is correlated with the corresponding changes in sample composition by well-known multivariate methods such as Partial Least Squares (PLS). The cross-correlation of the regression vector generated by PLS (shown in FIG. 7) and the sample spectrum is predictive of the analyte concentration. FIG. 8 shows a regression vector calculated by PLS for the prediction of YFP concentration. The cross-correlated intensity of this regression vector with the sample spectra are highly predictive of YFP concentration even when there are large changes in non-YFP sample component concentrations, as shown in FIG. 8.

Figure 7:
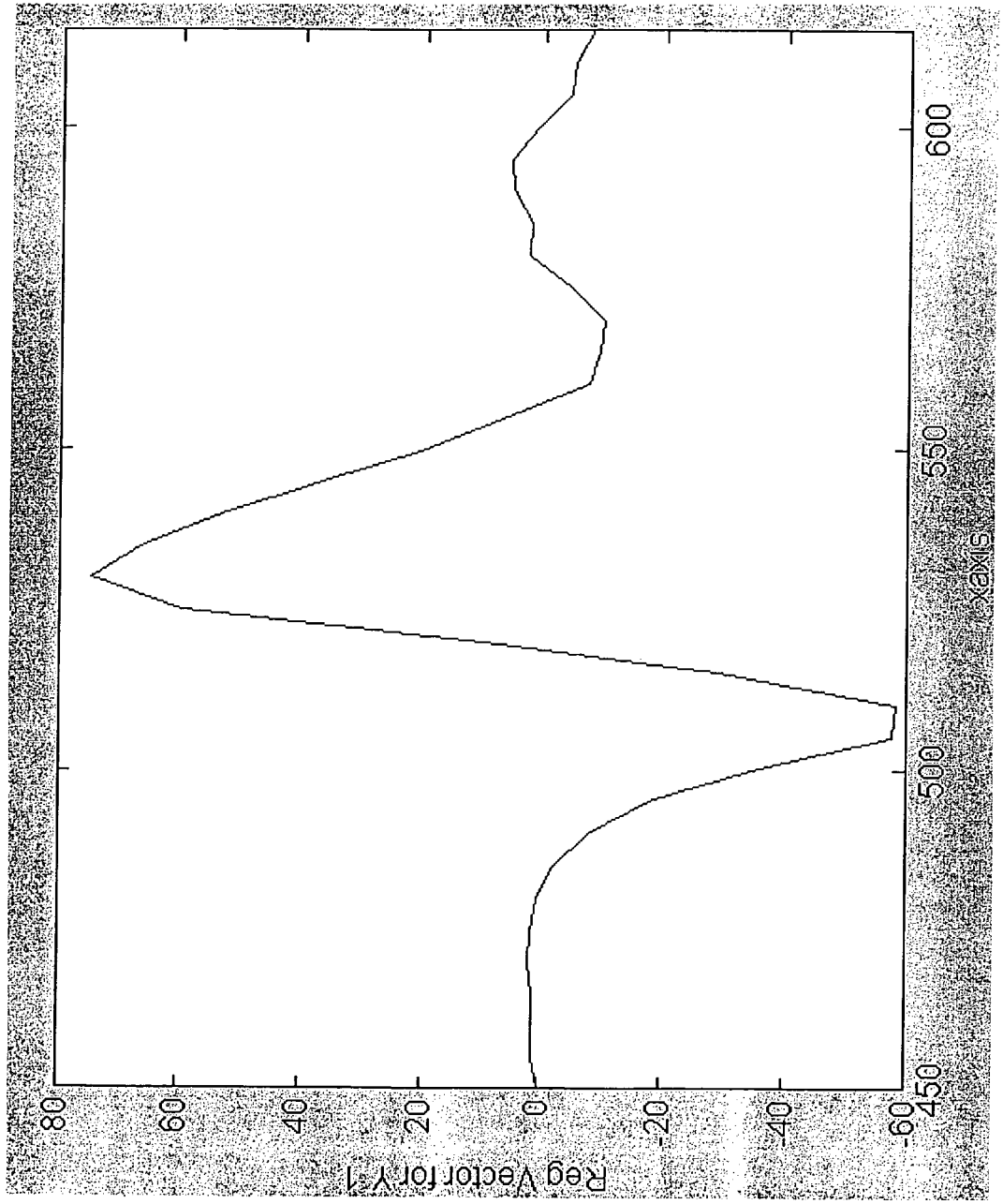
FIG. 7 depicts a PLS regression vector for predicting YFP concentration in mixtures.
Figure 8:
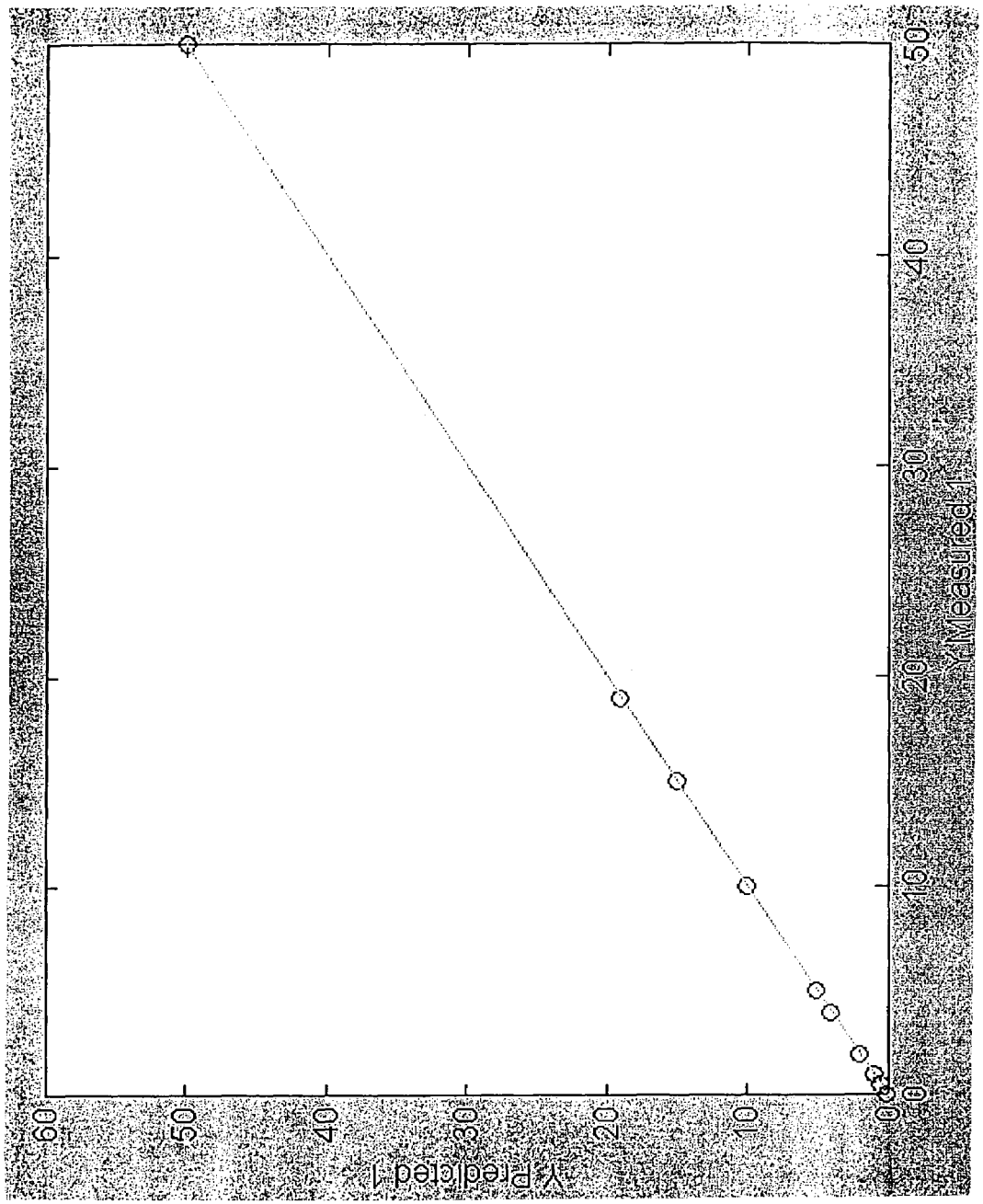
FIG. 8 depicts a calibration curve using the PLS regression vector from FIG. 7.

As shown in FIG. 7 the PLS regression vector contains negative intensity, however, which cannot be represented by the APS detector. The negative intensity of the regression vector can be made positive without loss of predictive power by adding a single constant value to each point in the regression vector. The resulting plots of cross-correlation intensity vs. analyte concentration remain linear, but with an increased y-intercept.

The dynamic reconfigurability of the user-defined functions of the current analysis system allows the concentration of different analytes to be to be determined. For example, multiple target species can be identified and analyzed on two or more rows of, or multi-dimensional APS array of pixels. The detector can be at the output plane of an imaging spectrometer that disperses the spectrum of the input across the detector. In such an embodiment, a row of pixels is a duplicate spectrum that can be cross-correlated with a different set of user-defined functions, where each set is associated with an independent target species, to provide analysis of different target species. A separate read operation is performed for each target species analyzed. In this example, each pixel has the same integration time and the same viewing time regardless of the numbers of target species being analyzed.

Referring back to FIG. 3 the two-dimensional filtering implementation can also be used effectively in more complicated cases where there is significant overlap between spectral characteristics of each probe or species. In this case, multiple filters corresponding to each probe or species can be applied in parallel to simultaneously identify and measure the concentration of each separate species.

The two-dimensional filtering can also be used for shape and size identification in conjunction with spectral identification. This consists of carrying out two-dimensional correlation with a two-dimensional user-defined function template corresponding to the shape or size of a particle. In this case, the each filter is a two-dimensional filter $F_{i,j}$, having a two-dimensional user-defined function template and a two-dimensional inner product computational unit, carrying out two-dimensional filtering:

$$O = \sum_i \sum_j a_{i,j} \cdot v_{i,j}$$

EXAMPLES

As described above, in operation, the detector performs a real-time cross-correlation of a user-defined analytical function with the measured spectrum. The cross correlation is carried out by simultaneously multiplying the spectrum readouts from each selected pixel by its associated user-defined analytical function from the set of user-defined functions and serially summing the resulting products to produce the output 140 of FIG. 1, which is proportional to the target species concentration. To carry out these operations in accordance with the present invention, at least two pixels are required to form an array of pixels.

In one illustrative example of FIG. 2, the array 200 comprises 6 rows×10 columns of pixels. The selector 210 selects four pixels 201, 202, 204, 206 from the fourth row of the 2-D array 200 to capture the spectrum 150 within the emission band associated with the spectrum of target species A. The pixels simultaneously read-out the spectrum of the excited sample (as shown in FIG. 9A). The pixels may also place the read-outs in a memory for further manipulation. The central processor has programmed each programmable circuitry of the pixels 200 in accordance with associated user defined function to achieve bandpass filtering of the read-out spectrum. For pixels 201-206, user defined functions $a_1$-$a_4$ are assigned from the user defined function template 230. FIG. 9B illustrates the bandpass filters programmed in the programmable circuitry. FIG. 9C illustrates the filtered spectrum after passing through the bandpass of FIG. 9B. Thus, the gain of the bandpass associated with the user-defined functions are applied to the read-outs. The associated user-defined functions $a_2$-$a_5$ are simultaneously multiplied with the spectrum read-outs and the products are then serially summed as a single scalar output in a single binning instruction.

The next example demonstrates an application in flow cytometry, which utilizes hundreds to millions of pixels configured in multi-dimensional arrays in accordance with the present invention.

Flow cytometers deliver particles, such as cells, in an extremely small diameter stream to an inspection zone. One or more lasers are focused in the inspection zone. Elastically and inelastically scattered light from each particle passing through the inspection zone is collected and analyzed. An optional cell sorter can be included in the flow stream after the inspection zone to physically segregate the particles based on the light scattering signals generated in the inspection zone.

Commercially available flow cytometers are capable of analyzing 50,000 particles per second. They can analyze up to 13 fluorescence wavelengths and two inelastic scattering angles simultaneously for each particle. Up to 3 different laser beams can be focused at different points in the stream, providing fluorescence and inelastic scattering data at 3 different wavelengths for each particle.

High throughput screening, combinatorial chemical synthesis, and advanced nanosensor technologies all benefit from being able to put multiple fluorescent labels on particles and then sort the particles based on the particular combination of labels present. The multiple labels can be thought of as a particle "bar code." Given that the useful spectral region for fluorescence emission from currently used fluorescent labels ranges from about 360 nm to about 1000 nm, and that spectral shifts as small as 5 nm to provide useful label discrimination, 128 simultaneous fluorescence wavelengths would be desirable for flow cytometry. In addition, label fluorescence changes with excitation wavelength. Accordingly, the use of multiple excitation wavelengths further multiplies the number of measurement channels, and therefore the potential information content of the fluorescence "bar code" that could be used to label a particle. Presently available flow cytometers measuring 13 fluorescence wavelengths can utilize only a small fraction of the information that can be placed into the fluorescence "bar code" because larger numbers of measurement channels become prohibitive when using single element detectors.

Particle sorting based on shape and size is also possible by analyzing elastically scattered light intensity as a function of angle. Many different angles would need to be measured to correctly classify asymmetric particles, despite the orientating effect of particle delivery devices (like a sheath flow cuvette). Again, a large number of measurement channels become prohibitive when using single element detectors.

Accordingly, an array detector readout speed of well over 10 megapixels/sec is needed to analyze 200 wavelength or scattering angle channels 50,000 times per second. This data flow then needs to be processed in real time. The detector of the current invention provides the detection and data flow rates required for flow cytometry using more than 200 information channels.

The present system enables 10 MHz update rates based on a computation speed of $10^9$ correlations per sec for 100 regions consisting of 9×9 cross-correlation blocks or 81 linear channels. Thus, cross-correlation of a user-defined function 5 rows with 50 channels/row with pixel data from 50 columns and 5 rows of pixels could be performed in approximately 500 ns.

In addition, a 2-dimensional compatibility with CMOS technology enables integration of digital timing and control with analog and digital signal processing, as well as Analog-to-Digital Converter (ADC) circuits on the same chip as the detector. Dynamically addressable random access enables fast readout of only windows of interest. The user-defined functions can then provide threshold or event detection. They can also be dynamically altered, giving a versatile integrated detector/signal processor. The result is the availability of low-cost, low power, high speed imagers exhibiting random access, simple digital interface, simplicity of operation and miniaturization through on-chip integration.

Although the present analysis system operates statically, where the user-defined function is statically configured by a user in accordance with a desired analysis scheme, the present analysis system can also be implemented dynamically. For example, the present analysis system can be taught to recognize desired targets with training sets and neural net software, thus, alter or reconfigure the user-defined functions optimally by itself without requiring the user's input.

Although specific embodiments are disclosed herein, it is expected that persons skilled in the art can and will design alternative spectral analysis devices that are within the scope of the following claims either literally or under the Doctrine of Equivalents.

What is claimed is:

1. A reconfigurable detector comprising:
   at least one array of a plurality of pixels, each of the plurality of pixels selected to receive and read-out an input, wherein the pixel array is divided into at least one pixel group for conducting a common predefined analysis, wherein each of the pixel groups is comprised of at least two pixels;
   each of the plurality of pixels having a programmable circuitry, in communication therewith, each of said circuitry being programmed with a dynamically configurable user-defined function such that each of said circuitry receives the input from the selected pixel and outputs a modified input; and
   a summing circuit in communication with the plurality of programmable circuits, said summing circuit designed to sum the modified inputs from the common pixel group in a single binning instruction to generate a scalar output for the pixel group,
   wherein the user-defined function comprises a function to selectively pick out a spectrum of a desired target, the user-defined function being determined by Partial Least Square (PLS) analysis followed by eigenvector rotation.

2. The reconfigurable detector of claim 1, wherein the pixel array is a one-dimensional array.

3. The reconfigurable detector of claim 1, wherein the pixel array is a two dimensional array.

4. The reconfigurable detector of claim 1, wherein the input comprises a spectrum selected from the group consisting of samples of interest from flowing streams, bead assays, cells, tagged cells, and raster-scanned static samples.

5. The reconfigurable detector of claim 4, wherein the spectrum comprises a fluorescence spectrum.

6. The reconfigurable detector of claim 4, wherein the spectrum comprises different light scattering angles from the samples of interest.

7. The reconfigurable detector of claim 4, wherein the spectrum comprises different Fourier frequencies of an image from the samples of interest.

8. The reconfigurable detector of claim 4, wherein the spectrum comprises a light spectrum.

9. The reconfigurable detector of claim 4, wherein the modification of the received input comprises cross-correlation of the received spectrum with the respective user defined function for each selected pixel.

10. The reconfigurable detector of claim 9, wherein the cross-correlation comprises simultaneously multiplying the received spectrum with the user-defined function for each selected pixel and serially summing the product to generate the single scalar output.

11. The reconfigurable detector of claim 1, wherein the array of the plurality of pixels comprises an active pixel sensor.

12. The reconfigurable detector of claim 1, wherein each pixel from the array of the plurality of pixels comprises a uniquely configured bandpass filter and a detector.

13. The reconfigurable detector of claim 1, wherein the read-out of the received input is placed in a dynamically addressable random access memory before the modification.

14. The reconfigurable detector of claim 1, wherein the detector has at least two pixel groups each having at least two pixels, and wherein each pixel group has a plurality of independent user defined functions associated therewith.

15. The reconfigurable detector of claim 1, wherein the programmable circuitry is integrated within the array of the plurality of pixels.

16. The reconfigurable detector of claim 1, wherein the programmable circuitry is separately arranged from the array of the plurality of pixels.

17. The reconfigurable detector of claim 1, wherein the programmable circuitries of the pixel group collectively comprise a user-defined function template and an inner product computational unit.

18. The reconfigurable detector of claim 17, wherein the array of the plurality of pixels, the user-defined function template, and the inner product computational unit are integrated on the same chip.

19. The reconfigurable detector of claim 17, wherein the array of the plurality of pixels, the user-defined function template, and the inner product computational unit are integrated via connections between a plurality of chips.

20. The reconfigurable detector of claim 19, wherein the array of the plurality of pixels, the user-defined function template, and the inner product computational unit are integrated via connections between a plurality of chips using bump bonding.

21. The reconfigurable detector of claim 19, wherein the array of the plurality of pixels, the user-defined function template, and the inner product computational unit are integrated via connections between a plurality of chips using 3-D chip integration.

22. The reconfigurable detector of claim 17, wherein the inner product computational unit performs inner product computation simultaneously during a signal integration time.

23. The reconfigurable detector of claim 17, wherein the inner product computational unit performs inner product computation prior to readout of the input.

24. The reconfigurable detector of claim 1, further comprising at least one of the circuits selected from the group consisting of digital control, timing logic, analog processing, and communication circuits.

25. A reconfigurable detector for simultaneously detecting a plurality of targets, the detector comprising:

at least one array of a plurality of pixels, each of the plurality of pixels selected to receive and read-out an input, wherein the pixel array is divided into at least one pixel group for conducting a common predefined analysis, wherein each of the pixel groups is comprised of at least two pixels;

each of the plurality of pixels having at least two programmable circuitries designed to simultaneously perform calculations to detect the plurality of targets, in communication therewith, each of said circuitries being programmed with a dynamically configurable user-defined function associated with a target species such that each of said circuitries receives the input from the selected pixel and outputs a modified input; and at least two summing circuits associated with the plurality of programmable circuitries and designed to simultaneously generate outputs representative of the plurality of targets, each of said summing circuits designed to sum the modified inputs from the associated one of the programmable circuitries to simultaneously generate a scalar output representative of the desired target, wherein the user-defined function comprises a plurality of user-defined functions to selectively pick out the plurality of desired targets, the user-defined function being determined by Partial Least Square (PLS) analysis followed by eigenvector rotation.

26. The reconfigurable detector of claim 25, wherein the pixel array is a one-dimensional array.

27. The reconfigurable detector of claim 25, wherein the pixel array is a two dimensional array.

28. The reconfigurable detector of claim 25, wherein the input comprises a spectrum selected from the group consisting of samples of interest from flowing streams, bead assays, cells, tagged cells, and raster-scanned static samples.

29. The reconfigurable detector of claim 28, wherein the spectrum comprises a fluorescence spectrum.

30. The reconfigurable detector of claim 28, wherein the spectrum comprises different light scattering angles from the samples of interest.

31. The reconfigurable detector of claim 28, wherein the spectrum comprises different Fourier frequencies of an image from the samples of interest.

32. The reconfigurable detector of claim 28, wherein the spectrum comprises a light spectrum.

33. The reconfigurable detector of claim 25, wherein the array of the plurality of pixels comprises an active pixel sensor.

34. The reconfigurable detector of claim 25, wherein each pixel from the array of the plurality of pixels comprises at least two uniquely configured multi-dimensional bandpass filters.

35. The reconfigurable detector of claim 25, wherein the read-out of the received input is placed in a dynamically addressable random access memory before the modification.

36. The reconfigurable detector of claim 25, wherein the detector has at least two pixel groups each having at least two pixels, and wherein each pixel group has a plurality of independent user defined functions associated therewith.

37. The reconfigurable detector of claim 25, further comprising at least one of the circuits selected from the group consisting of digital control, timing logic, analog processing, and communication circuits.

38. The reconfigurable detector of claim 25, wherein the programmable circuitries are integrated within the array of the plurality of pixels.

39. The reconfigurable detector of claim 25, wherein the programmable circuitries are separately arranged from the array of the plurality of pixels.

40. The reconfigurable detector of claim 25, wherein the programmable circuitries of the pixel group collectively comprise at least two user-defined function templates and at least two inner product computational units, wherein each of the at least two programmable circuitries of each pixel in the pixel group is independently associated with one of the user-defined function templates and the inner product computational units.

41. The reconfigurable detector of claim 40, wherein the array of the plurality of pixels, the user-defined function templates, and the inner product computational units are integrated on the same chip.

42. The reconfigurable detector of claim 40, wherein the array of the plurality of pixels, the user-defined function templates, and the inner product computational units are integrated via connections between a plurality of chips.

43. The reconfigurable detector of claim 42, wherein the array of the plurality of pixels, the user-defined function templates, and the inner product computational units are integrated via connections between a plurality of chips using bump bonding.

44. The reconfigurable detector of claim 42, wherein the array of the plurality of pixels, the user-defined function templates, and the inner product computational units are integrated via connections between a plurality of chips using 3-D chip integration.

45. The reconfigurable detector of claim 40, wherein the inner product computational units perform inner product computation simultaneously during a signal integration time.

46. The reconfigurable detector of claim 40, wherein the inner product computational units perform inner product computation prior to readout of the input.

47. The reconfigurable detector of claim 40, wherein the user-defined function templates and the computational units are two-dimensional.

48. The reconfigurable detector of claim 25, wherein the at least two summing circuits, each of said summing circuits sequentially generates a single scalar output representative of the plurality of targets.

* * * * *